United States Patent [19]

Bliem et al.

[11] Patent Number: 5,453,429
[45] Date of Patent: Sep. 26, 1995

[54] CROSSLINKED ANION EXCHANGE PARTICLES AND METHOD FOR PRODUCING THE PARTICLES

[75] Inventors: Paul E. Bliem, Pottstown, Pa.; Larry W. Steffier, Cherry Hill, N.J.

[73] Assignee: Rohm and Haas Company, Philadelphia, Pa.

[21] Appl. No.: 384,099

[22] Filed: Feb. 6, 1995

Related U.S. Application Data

[62] Division of Ser. No. 185,534, Jan. 24, 1994, Pat. No. 5,414,068.

[51] Int. Cl.$^6$ ........................................ A01N 43/42
[52] U.S. Cl. .................. 514/288; 424/78.1; 424/78.12; 424/497; 522/173; 526/310; 526/328.5; 514/554; 514/570
[58] Field of Search ........................... 514/288, 554, 514/570; 424/78.1, 78.12, 497; 522/173; 526/310, 328.5

[56] References Cited

U.S. PATENT DOCUMENTS

| | | | |
|---|---|---|---|
| 3,383,281 | 5/1968 | Wolf et al. | 424/78.12 |
| 3,692,895 | 9/1972 | Nelson et al. | 424/78 |
| 4,046,750 | 9/1977 | Rembaum | 526/310 |

*Primary Examiner*—Samuel A. Acquah
*Attorney, Agent, or Firm*—Thomas J. Howell

[57] ABSTRACT

New bile acid sequestrant polymer compositions and a process for preparing the polymers in particulate form, preferably in spherical form, are described. The polymer particles are prepared by crosslinking an amine-containing polymer with an amount of a polyfunctional amine-reactive compound sufficient to crosslink the polymer so that it is essentially water insoluble and has bile acid sequestering efficacy greater than that of cholestyramine, preferably greater than about three times the efficacy of cholestyramine. A preferred polymerization process involves suspension polymerization of water-soluble amine-containing monomers, such as dialkylaminoalkyl (meth)acrylate esters and dialkylaminoalkyl (meth)acrylamides, in the presence of polyfunctional amine-reactive compounds, such as substituted dihaloalkanes. Pharmaceutical compositions containing the bile acid sequestrant polymer particles and a method for lowering blood cholesterol levels using the pharmaceutical compositions are also described.

10 Claims, No Drawings

CROSSLINKED ANION EXCHANGE PARTICLES AND METHOD FOR PRODUCING THE PARTICLES

This is a divisional of application Ser. No. 08/185,534, filed Jan. 24, 1994, now U.S. Pat. No. 5,414,068.

BACKGROUND OF THE INVENTION

It has been recognized that elevated levels of cholesterol in the blood plasma are a major risk factor of coronary heart disease in humans and that reducing plasma cholesterol level decreases the risk of coronary heart disease. Successful approaches to controlling blood cholesterol levels have included dietary modification, e.g., minimizing the intake of cholesterol-laden foods and of foods having high fat content, inhibiting cholesterol biosynthesis and encouraging an increase in the amount of bile acids eliminated by the body.

Particulate resins, e.g., cholestyramine, described in U.S. Pat. No. 3383281, and colestipol, described in U.S. Pat. No. 3692895, that are capable of sequestering bile acids are known. Such resins, when orally administered to a mammalian host, form complexes with bile acid conjugates in the intestine and are effective in blocking resorbtion of bile acids from the intestine. The resin and sequestered bile acids are subsequently excreted from the body in fecal matter thereby increasing the rate at which bile acids are eliminated from the body. Other factors being equal, an increase in the rate at which bile acids are eliminated from the body tends to lower plasma cholesterol level by accelerating the conversion of cholesterol to bile acids in order to maintain a constant supply of bile acids in the body. A portion of the cholesterol for this increased synthesis of bile acids is supplied by removal of cholesterol from the blood plasma.

The bile acid sequestrants may be orally administered in various forms, typically as mixtures with food. Although the dosages of known sequestrants that are effective in lowering serum cholesterol in humans typically fall in the range of 10 to 15 grams/day, dosages of up to about 50 grams/day may be required. The particulate bile acid sequestrant resins can be unpleasant to ingest, particularly when large dosages are required and adverse side reactions (bloating, gas formation, constipation, diarrhea and the like) are common among patients to whom the resins are administered.

There has been a continuing effort in this field to minimize the unpleasant side effects associated with a therapeutically effective bile acid sequestrant regimen by developing sequestrants having increased ability to sequester bile acids and which are also effective in reducing serum cholesterol when administered at lower dosages than presently required using cholestyramine and colestipol.

While new candidate bile acid sequestrants must possess satisfactory bile acid sequestering efficacy, they must also be non-toxic to the host receiving the treatment. Some bile acid sequestrants may possess satisfactory bile acid sequestering efficacy, e.g., water-soluble polymers, however, they have been found to be cytotoxic towards the host due to sensitivity of living tissue exposed to the water-soluble bile acid sequestrant. It is, therefore, desirable to provide a bile acid sequestrant that possesses the bile acid sequestering efficacy of such water-soluble polymers but without the cytotoxic side effects which occur due to intimate contact between the sequestrant used and the living tissues exposed to the sequestrant.

One approach to providing bile acid sequestrants having the proper combination of physical properties is to polymerize functionalized monomers which are water-soluble due to their functionalized nature and to crosslink the polymer to such an extent to render it water-insoluble, thus minimizing cytotoxic effects, without hindering accessibility of the functionalized sites of the sequestrant to target bile acids to be removed.

It is an object of the present invention to provide a bile acid sequestrant with enhanced bile acid sequestering efficacy and low mammalian cytotoxicity based on a crosslinked polymer made from functionalized water-soluble monomers. Another object of the invention is to provide a process for preparing the bile acid sequestrant polymer particles, preferably as spherical polymer particles.

SUMMARY OF THE INVENTION

The present invention provides essentially water-insoluble bile acid sequestrant polymer particles in the form of anion exchange resins and a process for preparing the polymer particles comprising (a) polymerizing a monomer mixture comprised of amine-containing monomers by free radical polymerization and (b) non-free-radical crosslinking with a polyfunctional amine-reactive compound, to provide polymer particles that have bile acid sequestering efficacy greater than that of cholestyramine.

In one aspect of the invention the polymerization process comprises suspension polymerization of water-soluble amine-containing monomers, optionally using a sufficient amount of a dispersant to provide the polymer particles in spherical form. Another aspect of the invention involves conducting the polymerization wherein crosslinking with polyfunctional amine-reactive compounds occurs during formation of the polymer particles.

In another aspect of the invention polymer compositions are provided that comprise bile acid sequestrant polymer particles prepared according to the aforementioned process, for example, wherein the amine-containing monomer is an unsubstituted or substituted aminoalkyl (meth)acrylate ester or an unsubstituted or substituted aminoalkyl (meth)acrylamide; and the polyfunctional amine-reactive compound is selected from unsubstituted or substituted members of the following classes: dihaloalkanes, aralkyl dihalides, alkylene diesters, aryl diesters, aralkyl diesters, alkylene diacylhalides, aryl diacylhalides, aralkyl diacylhalides, dialdehydes, diepoxyalkanes, epihalohydrins and aralkyl diepoxides.

In another aspect of the invention polymer compositions are provided that comprise bile acid sequestrant polymer particles that have amine functionality attached to polymer backbone through a side chain linkage group. In yet another aspect the polymer compositions comprise polymer particles that are in the form of a pharmaceutically acceptable salt.

The present invention provides pharmaceutical compositions comprising a therapeutically effective amount of the polymer composition of the bile acid sequestrant polymer particles and a pharmaceutically acceptable carrier.

The present invention also provides a method for lowering blood cholesterol level in a mammal comprising oral administration to the mammal of a therapeutically effective amount of the bile acid sequestrant polymer particles prepared according to the aforementioned process.

DETAILED DESCRIPTION OF THE INVENTION

The anion exchange resins of the present invention may be prepared by several variations of the same process. In one variation the polymers may be produced by bulk polymerization in which the amine-containing monomer is first mixed with a monomer-soluble polyfunctional amine-reactive compound; the mixture is then heated, for example on a heated plate, roll or sheet, to polymerize the mixture to a solid mass, after which the solid polymer is granulated into particles by grinding, flaking or other similar means.

In another variation the polymers may be produced wherein polymerizing a monomer mixture comprising amine-containing monomers by free radical polymerization is completed to produce an uncrosslinked polymer, followed by non-free-radical crosslinking with a polyfunctional amine-reactive compound to form the crosslinked polymer particles. Preferably, this type of polymer is prepared in aqueous solution and the resultant polymer may be further granulated to the desired particle size by grinding and similar procedures.

In yet another variation the polymers of the invention are produced by suspension polymerization, preferably in aqueous media. A monomer mixture of one or more water-soluble, amine-containing monomers, optionally containing one or more additional, copolymerizable monomers, together with a monomer-soluble polyfunctional compound having functional groups capable of reacting with amine functional groups of the amine-containing monomer, is suspended in an aqueous medium and the suspension is polymerized in the presence of a monomer-soluble, free-radical initiator to form polymer particles which have amine functionality. Preferably suspension aids are used to provide polymer particles in spherical form; for example, the aqueous phase may contain dissolved inorganic salts and suitable dispersants.

In a preferred embodiment of the invention the process comprises suspension polymerizing a monomer mixture comprised of water-soluble amine-containing monomers by free radical polymerization using a dispersant to provide the polymer particles in spherical form, and non-free-radical crosslinking with a polyfunctional amine-reactive compound during formation of the particles to provide polymer particles that (1) have bile acid sequestering efficacy greater than that of cholestyramine and (2) that have amine functionality attached to polymer backbone through a side chain linkage group. A more preferred embodiment of the polymer particles is in the form of a pharmaceutically acceptable salt having bile acid sequestering efficacy at least three times the efficacy of cholestyramine.

As used herein, the terms "(meth)acrylate" and "(meth)acrylamide" refer to either the corresponding acrylate or methacrylate and acrylamide or methacrylamide, respectively. Also, as used herein, the term "substituted" is used in conjunction with various amine-containing monomers and polyfunctional amine-reactive compounds to indicate that one or more hydrogens of these compounds has been replaced, for example, with ($C_1$-$C_8$)alkyl, halogen (e.g., chloro-, bromo-), hydroxyl groups and the like, except where such groups may be incompatible with functional groups already present.

Among those amine-containing monomers suitable for use in the present invention are those vinyl monomers containing amine functionality that is not directly attached to the vinyl group. Such monomers include, for example, amide monomers such as dialkylaminoalkyl acrylamides or methacrylamides (for example, dimethylaminopropyl methacrylamide), N,N-bis-(dimethylaminoalkyl) acrylamides or methacrylamides, N-β-aminoethyl acrylamide or methacrylamide, N-(methylaminoethyl)acrylamide or methacrylamide, aminoalkylpyrazine acrylamides or methacrylamides; acrylic ester monomers such as dialkylaminoalkyl acrylates or methacrylates (for example, dimethylaminoethyl acrylate or methacrylate), β-aminoethyl acrylate or methacrylate, N-(n-butyl)-4-aminobutyl acrylate or methacrylate, methacryloxyethoxyethylamine, and acryloxypropoxypropoxypropylamine; vinyl monomers such as vinyl pyridines; aminoalkyl vinyl ethers or sulfides such as β-aminoethyl vinyl ether, β-aminoethyl vinyl sulfide, N-methyl-β-aminoethyl vinyl ether or sulfide, N-ethyl-β-aminoethyl vinyl ether or sulfide, N-butyl-β-aminoethyl vinyl ether or sulfide, and N-methyl-3-aminopropyl vinyl ether or sulfide; N-acryloxyalkyl-oxazolidines and N-acryloxyalkyltetrahydro-1,3-oxazines such as oxazolidinylethyl methacrylate, oxazolidinylethyl acrylate, 3-(γ-methacryloxypropyl)tetrahydro-1,3-oxazine, 3-(β-methacryloxyethyl)-2,2-pentamethylene-oxazolidine, 3-(β-methacryloxyethyl)-2-methyl-2-propyloxazolidine, N-2-(2-acryloxyethoxy)ethyl-oxazolidine, N-2-(2-methacryloxyethoxy)-ethyl-5-methyl-oxazolidine, 3-[2-(2-methacryloxyethoxy)ethyl]-2,2-dimethyloxazolidine, N-2-(2-acryloxyethoxy)ethyl-5-methyl-oxazolidine, 3-[2-(methacryloxyethoxy)ethyl]-2-phenyl-oxazolidine, N-2-(2-methacryloxyethoxy)ethyl-oxazolidine, and 3-[2-(2-methacryloxyethoxy)ethyl]-2,2-pentamethylene-oxazolidine.

Preferred water-soluble, amine-containing monomers useful in the present invention are unsubstituted or substituted aminoalkyl (meth)acrylate esters and unsubstituted or substituted aminoalkyl (meth)acrylamides. Included among these monomers are: dimethylaminoalkyl acrylamides and methacrylamides, N,N-bis-(dimethylaminoalkyl) acrylamides and methacrylamides, dimethylaminoalkyl acrylates and methacrylates, or mixtures including any of these monomers. Most preferred are the dimethylaminoalkyl acrylamides and methacrylamides, dimethylaminoalkyl acrylates and methacrylates and mixtures thereof in which the alkyl group has front 2 to about 8 carbon atoms, and particularly preferred are dimethylaminopropyl methacrylamide, dimethylaminoethyl methacrylate and mixtures thereof. The water-soluble monomer is present in the monomer mixture as the major component; that is, the water-soluble monomer or monomers are present at a level of at least 50 weight percent by weight of the total monomers. As used herein, the term "water-soluble," as applied to monomers, indicates that the monomer has a solubility of at least about 1 gram per 100 grams of water, preferably at least about 10 grams per 100 grams of water, and more preferably at least about 50 grams per 100 grams of water.

Other, non-amine-containing, monomers may optionally be present as minor components of the monomer mixture; that is, they may be present in a total combined amount of less than about 50% by weight of the total monomer mixture. Such non-amine-containing monomers are preferably present at less than about 25% by weight of the total monomer mixture. The non-amine-containing monomers useful in the present invention include those which are copolymerizable with the water-soluble monomer. Examples of such other monomers include, but are not limited to, aromatic monomers such as styrene and α-methylstyrene, and aliphatic monomers such as methyl acrylate, methyl methacrylate, ethyl acrylate, ethyl methacrylate, butyl acrylate, butyl methacrylate, maleic anhydride, vinyl acetate and the like, and mixtures thereof.

In addition to the presence of non-amine-containing monomers, inert solvents may also be present in the monomer mixture; that is, they may be present at less than about 80%, preferably less than about 50% by weight of the total monomer mixture. Such inert solvents are preferably present at less than about 25% by weight of the total monomer mixture. Preferred inert solvents useful in the present invention include those which are themselves water-insoluble, but which are miscible with the water-soluble monomer. The inert solvents that combine the properties of water-insolubility and monomer-solubility are especially useful for enhancing the integrity of the spherical beads formed during the suspension polymerization of the water-soluble amine-containing monomers. Examples of such other solvents include, but are not limited to, hexane, heptane, isooctane, toluene, xylene, ethylbenzene and mixtures thereof.

Crosslinkers of the general formula B react with amine functionality, $NRR^1$, of the amine-containing polymer (represented in part by structure A) or the corresponding amine-containing monomer to produce crosslinked polymer (represented in part by structure C) according to Equation 1:

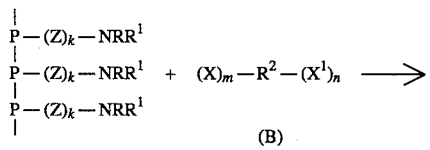

(A)

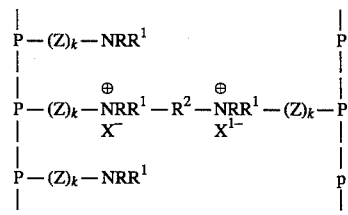

(C)

where

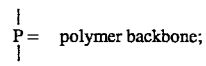 polymer backbone;

Z=side chain linkage group;

k, m, n=zero or an integer from 1 to 3, and may be the same or different;

R, $R^1$=($C_1$-$C_8$)alkyl groups or hydrogen; or R and $R^1$ together with the nitrogen atom to which they are attached may be joined to form a saturated ring, optionally containing one or more further hetero-atoms, for example oxygen or nitrogen;

$R^2$=($C_1$-$C_{20}$)alkylene, aryl, ($C_8$-$C_{20}$)aryl-bis-alkylene

X, $X^1$=halogen, tosylate, mesylate, brosylate, nosylate, triflate, nonaflate, tresylate, epoxide (X or $X^1$ is attached to $R^2$ in C as —O⁻), and may be the same or different.

The side chain linkage group, Z, is any chemically stable linkage between —$NRR^1$ and the polymer backbone, i.e., —$NRR^1$ is not attached directly to polymer backbone. By "chemically stable" is meant that Z does not substantially decompose or degrade during the polymerization or crosslinking reactions. When k is zero the amine functionality is attached directly to the polymer backbone. Types of side chain linkage groups suitable for use in the present invention include, for example:

an oxyalkylene group: —O—(CHR)$_x$—, a thioalkylene group: —S—(CHR)$_x$—, an alkylaminoalkyl group: —(CHR)$_x$—NR—(CHR)$_x$—, an alkylene group: —(CHR)$_x$—, an arylalkylene group: —$C_6H_4$—(CHR)$_x$—, an alkoxyalkyl group: —(CHR)$_x$—O—(CHR)$_x$—, an alkylthioalkyl group: —(CHR)$_x$—S—(CHR)$_x$—(and corresponding sulfone and sulfoxide derivatives), an amidoalkyl group: —C(=O)NR—(CHR)$_x$—, a carboxyalkyl group: —C(=O)O—(CHR)$_x$—, where R is as defined above and x is an integer from 1 to 10. When n=m=1, the polyfunctional amine-reactive compound is represented by a difunctional crosslinker. Sulfur and nitrogen atoms present in the side chain linkage may participate in the crosslinking reaction with polyfunctional amine-reactive compounds depending on the reactivities of the particular materials involved.

When neither R nor $R^1$ in Equation 1 is hydrogen, then the crosslinking sites in the resultant polymer are represented by the quaternary ammonium salt form as illustrated in structure C. When R or $R^1$ is hydrogen, the crosslinking sites in the resultant polymer (represented in part by structure C') may be partially or totally in the free base form in the presence of excess amine functionality.

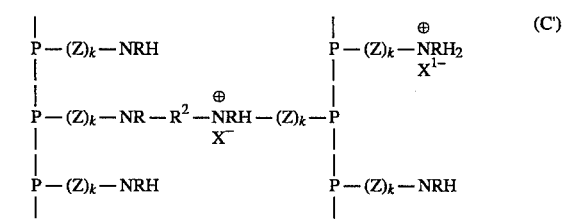

When the polyfunctional amine-reactive compound is a diester (B', where Y, $Y^1$= carbalkoxy, represented by —$COOR^3$) or diacid chloride (B', where Y, $Y^1$=haloacyl, represented by —$COY^2$), at least one R or $R^1$ of A=hydrogen, $R^3$=($C_1$-$C_8$)alkyl, and $Y^2$ =halogen, then the crosslinking reaction takes place according to Equation 2. When B' is a diacid chloride some portion of the amine functionality in the resultant crosslinked polymer (represented in part by structure D) will be in the $HY^2$ salt form and when B' is a diester the amine functionality will be in the free base form with $R^3OH$ as a byproduct of the crosslinking reaction.

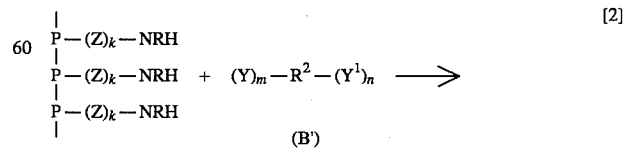

(A)

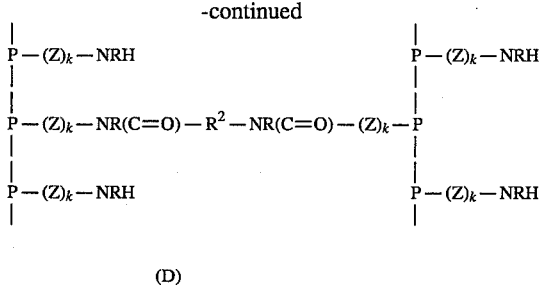

(D)

When at least some of the amine functionality in A is represented by both R and $R^1$ being hydrogen, then dialdehydes may be used to crosslink the polymer. In this case, the resultant crosslinked polymer contains imine groups, known as Schiff bases when the dialdehyde is an aromatic dialdehyde, such as isophthalaldehyde, phthalaldehyde or terephthalaldehyde. Glutaraldehyde is an example of a suitable aliphatic dialdehyde.

When R or $R^1$ is hydrogen, or both R and $R^1$ are hydrogen, a Michael-type reaction (also known as conjugate addition) may be used to crosslink the polymer in the absence of free-radical polymerization conditions. Examples of crosslinkers suitable for crosslinking the polymer in this manner are ethyleneglycol diacrylate, ethyleneglycol dimethacrylate, trimethylolpropane triacrylate, trimethylolpropane trimethacrylate and the like.

Crosslinkers useful in practicing the present invention are those compounds containing more than one amine-reactive site, i.e., any polyfunctional amine-reactive compound. Compounds suitable for use as crosslinkers in the present invention (designation B or B' in Equations 1 and 2) include unsubstituted and substituted members of the following classes: dihaloalkanes, aralkyl dihalides (such as bis(chloromethyl)benzene), alkylene diesters, aryl diesters, aralkyl diesters, alkylene diacylhalides (such as succinyl chloride), aryl diacylhalides, aralkyl diacylhalides, dialdehydes, diepoxyalkanes and aralkyl diepoxides. Polyfunctional amine-reactive compounds having mixed functional groups (where X and $X^1$ or Y and $Y^1$ are different), for example, epihalohydrins such as epichlorohydrin or epibromohydrin, are also suitable as crosslinkers. In addition, the tosylate (p-toluenesulfonate), mesylate (methanesulfonate), brosylate (p-bromobenzenesulfonate), nosylate (p-nitrobenzenesulfonate), triflate (trifluoromethanesulfonate), nonaflate (nonafluorobutanesulfonate), and tresylate (trifluoromethanesulfonate) derivatives of unsubstituted and substituted difunctional alkanes and aralkanes are suitable as crosslinkers in the present invention.

Preferred dihaloalkanes are dichloroalkanes and are represented, for example, by those selected from the group consisting of 1,2-dichloroethane, 1,2-dichloropropane, 1,3-dichloropropane, 1,3-dichloro-2-propanol and 1,4-dichlorobutane. Preferred alkylene diesters are dimethyl malonate, dimethyl succinate, diethyl glutarate, diethyl adipate, diethyl suberate, diethyl azelate and diethyl sebacate.

The amount of crosslinking provided by the polyfunctional amine-reactive compounds used in the polymers of the present invention may be any amount that is effective to render the polymer insoluble in water, e.g., from about 0.1 to about 50 mole percent, preferably from about 0.5 to about 20 mole percent of total monomers, while maintaining efficacy as a bile acid sequestrant. When the term "total monomers" is used in this context, reference is being made to both the amine-containing monomers and the polyfunctional amine-reactive compounds used as crosslinkers. Most preferably, the amount of crosslinking approaches the minimum amount effective to render the polymer insoluble in water, e.g., from about 2 mole percent to about 10 mole percent of total monomers present, while maintaining high efficacy as a bile acid sequestrant.

In addition to the polyfunctional amine-reactive crosslinker compounds, the polymers of the present invention may also be crosslinked with minor amounts of conventional free-radical reactive polyvinyl monomers, i.e., less than about 10 mole percent, preferably less than about 2 mole percent, and most preferably less than about 0.5 mole percent based on total monomers. Conventional polyvinyl monomers, which copolymerize under free-radical conditions, include, for example, divinylbenzene, trivinylbenzene, divinyltoluene, divinylpyridine, ethyleneglycol diacrylate, ethyleneglycol dimethacrylate, trimethylolpropane triacrylate, trimethylolpropane trimethacrylate, diethyleneglycol divinyl ether and the like.

While not wishing to be bound by theory, we believe that, in the case of the present invention, there is little or no heterogeneity incorporated into the polymer backbone since the crosslinker does not act as a free-radical reactive comonomer during the polymerization of the amine-containing monomer. Instead, the crosslinking reaction takes place at sites away front the polymer backbone by nucleophilic displacement reaction mechanisms. The process of the present invention provides a greater chance for random homogeneous distribution of the crosslinking sites in the resultant crosslinked amine-containing polymer particles when compared to conventional crosslinked particles prepared by free-radical copolymerization (such as cholestyramine and others prepared with polyvinyl comonomers) or by crosslinking directly through polymer backbone sites (such as colestipol). In addition to the more homogeneous distribution of crosslink sites, it is believed that the process of the present invention allows for (1) greater control over molecular dimensions of the crosslinking moiety and, subsequently, the molecular flexibility of the resultant crosslinked structure when compared to conventional crosslinked polymers, resulting in (2) bile acid sequestering efficacy greater than that of cholestyramine, preferably at least three times, and most preferably, at least four times the efficacy of cholestyramine.

The mechanism by which polymers of the present invention are crosslinked involves reaction between the nucleophilic amine groups of the polymer side chains with amine-reactive sites of the crosslinker molecule; these reactions may involve quaternization of the side chain amine groups or, in the case of primary or secondary amine groups, acylation, alkylation, condensation or conjugate addition reactions. The timing of the actual crosslinking reaction relative to the formation of polymer may vary depending upon the reactivity of the polyfunctional amine-reactive compound and the amine-containing monomer. Crosslinking may occur before, during or after the actual polymerization of the amine-containing monomer or any combination thereof. In the case of aqueous phase suspension polymerization, it is preferred that at least some of the crosslinking occurs during the polymerization of amine-containing monomer to facilitate the formation of water-insoluble spherical particles. Polymers of the present invention in the form of spherical particles are preferred because of the ease of handling during isolation, cleaning and washing of the polymer; however, other forms of the polymers, e.g., precipitation, powdered, etc., are equally efficacious regarding bile acid sequestering capacity.

Polymerization initiators useful in the present invention include monomer-soluble initiators such as peroxides, hydroperoxides and related initiators, as for example benzoyl peroxide, tert-butyl hydroperoxide, cumene peroxide, tetralin peroxide, acetyl peroxide, caproyl peroxide, tert-butyl peroctoate, tert-butyl perbenzoa te, tert-butyl diperphthalate, methyl ethyl ketone peroxide and the like. Also useful are azo initiators such as azodiisobutyronitrile, azodiisobutyramide, 2,2'-azo-bis(2,4-dimethylvaleronitrile), azo-bis(α-methylbutyronitrile) and dimethyl-, diethyl- or dibutyl azo-bis(methylvalerate). Preferred initiators are the azo initiators, and particularly preferred is 2,2'-azo-bis(2,4-dimethylvaleronitrile). Preferred use levels of peroxide and azo initiators are from about 0.01% to 3% by weight, and from about 0.01% to about 2% by weight, respectively, based on the total weight of vinyl monomers.

Salts useful for reducing solubility of the water-soluble monomer in the aqueous phase are water-soluble, non-reactive inorganic salts of a monovalent, divalent or aluminum cation and a monovalent or divalent anion, including, but not limited water-soluble, non-reactive inorganic salts of a monovalent, divalent or aluminum cation and a monovalent or divalent anion, as for example sodium, potassium, lithium and ammonium salts of chloride, bromide, iodide, sulfate, carbonate and nitrate and the magnesium and calcium salts of chloride, bromide, iodide and nitrate. Preferred salts are sodium chloride, sodium sulfate and sodium nitrate. The salt is dissolved in the aqueous medium at levels from about 5% by weight, based upon the total aqueous phase weight, to saturation of the salt in the aqueous phase. The term "non-reactive," as applied to the salts herein, means that the salt does not react chemically with water, the monomers or the polymers formed from the monomers.

The preferred dispersants useful for making the anion exchange resin particles of the present invention are nonionic surfactants having a hydroxyalkylcellulose backbone, a hydrophobic alkyl side chain containing from I to about 24 carbon atoms, and an average of from about 1 to about 8, preferably from about 1 to about 5, ethylene oxide groups substituting each repeating unit of the hydroxyalkylcellulose backbone, the alkyl side chains being present at a level of front about 0.1 to about 10 alkyl groups per 100 repeating units in the hydroxyalkylcellulose backbone. The alkyl group in the hydroxyalkylcellulose may contain from 1 to about 24 carbons, and may be linear, branched or cyclic. More preferred is a hydroxyethylcellulose containing front about 0.1 to about 10 ($C_{16}$)alkyl side chains per 100 anhydroglucose units and from about 2.5 to about 4 ethylene oxide groups substituting each anhydroglucose unit. A particular advantage of these dispersants is that the spherical polymer particles of the present invention produced using them are not agglomerated, i.e., clumps of particles do not adhere to one another; agglomeration occurs when unprotected or poorly protected particles collide during the polymerization process. Typical use levels of dispersants are from about 0.01 to about 4% by weight, based upon the total aqueous-phase weight.

Other dispersants useful for making the anion exchange resin particles of the present invention include finely divided particles such as silica, clays, ground ion exchange resins or ground, crosslinked, suspension copolymers without ion exchange functionality, and inorganic salts such as calcium hydroxyphosphate, particularly in combination with hydroxyapatite. The inorganic salts may or may not be fully soluble in water, and where they are not fully soluble they may behave similarly to the finely divided particles. Still other dispersants useful for making the anion exchange resin particles of the present invention are polymers containing hydrophilic backbones, which can orient their lipophilic portions to the monomer phase and their hydrophilic portions to the aqueous phase at the interface of the two phases. These polymeric dispersants include celluloses, polyvinyl pyrrolidones, polyvinyl alcohols, starches and the like. Mixtures of dispersants may also be used. These other dispersants tend to be less preferred, as they tend to produce a somewhat greater amount of agglomerated or otherwise undesirable material.

Bile acid sequestrant polymers of the present invention may be prepared in macroporous or macroreticular form according to known methods by conducting the polymerization in the presence of precipitants, such as those disclosed in Meitzner et al., U.S. Pat. No. 4256840. The precipitant may be present in ratios from about 20 parts per 100 parts of monomer, i.e., 20% on monomer, to about 600 parts per 1.00 parts of monomer, i.e., 600% on monomer, depending on the crosslinking level and precipitant used. Suitable precipitants for preparing macroporous or macroreticular polymers are those materials that are solvents for the monomer and non-solvents for the resultant crosslinked polymer. Preferred precipitants include: dialkyl ketones, e.g., methyl isobutyl ketone, diisobutyl ketone and the like; ($C_4$-$C_{10}$)alcohols, e.g., t-amyl alcohol, 2-ethylhexanol, methylisobutyl carbinol and the like; ($C_6$-$C_8$)alkanes, e.g., heptane, isooctane and the like; and ($C_7$-$C_{10}$)aromatic hydrocarbons, e.g., toluene, xylene and the like.

Uncrosslinked poly(dimethylaminopropylmethacrylamide), while exhibiting efficacy as a bile acid sequestrant (relative to cholestyramine), has shown evidence of toxicity when orally administered to rats, monkeys and dogs. The crosslinked bile acid sequestrants of the present invention exhibit reduced toxicity toward mammalian tissue relative to linear, i.e., uncrosslinked poly(dimethylaminopropylmethacrylamide).

Preferably, the bile acid sequestrants of the present invention exhibit anion exchange capacities of greater than about 3 milliequivalents per gram of dry polymer (meq/g) and, more preferably, greater than about 4 meq/g. Most preferably, the bile acid sequestrants of the present invention exhibit anion exchange capacities of about 5 meq/g to about 6 meq/g.

Bile acid sequestrants of the present invention may be used in the form of free bases or in the form of pharmaceutically acceptable acid salts, or mixtures thereof. Pharmaceutically acceptable acid salts are those whose anions, when used in therapeutically effective amounts, are nontoxic to the organism to whom the salts are administered. Examples of such salts are those derived from mineral acids such as hydrochloric and phosphoric, or organic acids such as acetic, citric, lactic and malonic. The various salt forms of the present invention may be prepared by dissolving the acid in a suitable solvent, e.g., water or a solution of water and an alcohol, treating the free base with the solution to form the salt and then isolating the insoluble salt from the solution.

Hydrated, i.e., water-swollen, particles exhibiting a mean particle diameter front about 10 microns to about 400 microns, preferably from about 10 to about 200 microns, are a preferred form of the polymers prepared by the process of the present invention for use as bile acid sequestrants.

In general, bile acid sequestrants of the present invention are used for lowering blood cholesterol level in a mammal by oral administration of a therapeutically effective amount of the bile acid sequestrant to the mammal. The dosage of the sequestrants that will be most suitable for reduction of blood cholesterol level will vary with the form of administration, the particular embodiment of sequestrant, and the physiological characteristics of the host to which the sequestrant is administered. In general the amount administered is between about 2 and about 125 milligrams per kilogram (mg/kg) of body weight of the mammal per day. Based on physiological studies with beagle dogs (as described in Example 5), it is expected that the therapeutic dosage in humans will generally be from about 2 to about 125 mg/kg of body weight per day. This would correspond to a dosage for an 80 kg human host of about 0.2 to about 10 grams/day. It is expected that more widely used dosages will be front about 35 to about 50 mg/kg of body weight per day corresponding to about 2.5 to about 4 grams/day for an 80 kg host.

Pharmaceutical compositions of the present invention are prepared by combining (1) a therapeutically effective amount of a polymer composition containing the bile acid sequestrant polymer particles with (2) a pharmaceutically acceptable carrier. Bile acid sequestrants of the present invention can be orally administered in any suitable way, including in neat form or in the form of pharmaceutical compositions in which the sequestrant is combined with pharmaceutically acceptable carriers, for example, in the form of tablets, capsules, particles, i.e., granules or powders, or as aqueous suspensions. In the case of tablets for oral use, commonly used carriers such as lactose and corn starch, and lubricating agents such as magnesium stearate, may be added. For oral administration in capsule form useful diluents include, e.g., lactose and dried starch. When aqueous suspensions are required for oral use the active ingredient is combined with emulsifying and suspending agents. If desired, sweetening and flavoring agents may be added. Particulate forms of the sequestrant may be administered as a mixture with food items such as applesauce, stewed fruits, juices and cereals.

Bile acid sequestrants of the present invention can be used in conjunction with other treatments that are designed to lower the level of cholesterol in the blood. Preferred pharmaceutical compositions comprise a sequestrant of the present invention used in combination with a therapeutically effective amount of a material that inhibits cholesterol biosynthesis. Examples of such materials would include but are not limited to HMG-coenzyme A (HMG-CoA) reductase inhibitors, HMG-CoA synthase inhibitors, squalene epoxidase inhibitors and squalene synthase inhibitors. More preferred pharmaceutical compositions comprise a HMG-CoA reductase inhibitor as the cholesterol biosynthesis-inhibiting material. Illustrative of such HMG-CoA reductase inhibitors are lovastatin, simvastatin, pravastatin and fluvastatin. Examples of HMG-CoA synthase inhibitors are β-lactone derivatives, β-lactam derivatives and substituted oxacyclopropane analogues. Other cholesterol level-lowering agents that may be administered in conjunction with the sequestrants of the present invention include niacin, probucol, the fibric acids (clofibrate and gemfibrozil) and LDL-receptor gene inducers.

The following examples are intended to illustrate the invention and not to limit it except as it is limited in the claims. All ratios and percentages given herein are by weight unless otherwise specified, and all reagents used in the examples are of good commercial quality unless otherwise specified.

EXAMPLE 1

This example illustrates the preparation of spherical crosslinked particles of the present invention from water-soluble dimethylaminopropyl methacrylamide (DMAPMAM) monomer that has been crosslinked with the difunctional amine-reactive compound 1,3-dichloropropane.

The dispersant used was a modified hydroxyethylcellulose which was characterized by substitution with about 4.0 moles of ethylene oxide per anhydroglucose unit and approximately 0.7–1.0 cetyl groups per 100 anhydroglucose units, a molecular weight of approximately 300,000 and a viscosity in 1% aqueous solution of approximately 400 megaPascals.

An aqueous solution was prepared by weighing 99.4 g sodium chloride, grinding approximately 6 g of this sodium chloride in a mortar with 1.5 g dispersant to a homogeneous mixture. The unground sodium chloride was added, with stirring, to 274.1 g deionized water at about 55° C. The ground sodium chloride-dispersant mixture was added slowly to the water, which was then stirred at 55° C. until all the solids had dissolved.

A monomer mixture was made by mixing 67.0 g DMAPMAM, 3.44 g 1,3-dichloropropane, 56.2 g o-xylene and 0.687 g 2,2'-azo-bis-(2,4-dimethylvaleronitrile). The difunctional amine-reactive compound content, based on the total monomer weight, was 5% (7.3 mole %).

The aqueous phase was placed in a 1-liter round-bottomed flask equipped with 2-blade agitator and stirred at 55° C. The monomer mixture was transferred to the reactor vessel and stirred while maintaining a temperature of 55° C. for 14 hours, after which the solids were drained free of liquid and washed three times with water to remove the salt and most of the xylene.

The washed resin was then dried under vacuum at 60° C. and ground to a particle size of less than about 200 μ. The recovery of dried resin was about 80–85%. Electron Spectroscopy for Chemical Analysis (ESCA) indicated the presence of charged (quaternary) nitrogen and neutral (amide+ amine) nitrogen.

EXAMPLE 2

This example illustrates the preparation of spherical crosslinked particles of the present invention from DMAPMAM monomer that has been crosslinked with the difunctional amine-reactive compound 1,3-dichloro-2-propanol.

The spherical copolymer beads of this example were prepared using the same procedure as that of Example 1, except that 121.8 g of DMAPMAM, 6.25 g of 1,3-dichloro-2-propanol, 1.25 g of 2,2'-azo-bis-(2,4-dimethylvaleronitrile) and no xylene were used. The difunctional amine-reactive compound content, based on the total monomer weight, was 5% (6.5 mole %). The recovery of dried resin was 116 g (93%). ESCA indicated the presence of charged (quaternary) nitrogen and neutral (amide+ amine) nitrogen.

EXAMPLE 3 (comparative)

In a manner similar to that of Example 1, a sample of crosslinked poly(dimethylaminopropylmethacrylamide) in the form of porous, spherical beads was prepared by copolymerizing DMAPMAM with a conventional polyvinyl crosslinker, divinylbenzene (DVB).

A monomer mixture was made by mixing DMAPMAM and DVB (55% active (by weight), 45% ethylvinylbenzene); no o-xylene was used. A mixed initiator solution (30% by weight in acetone) based on 2,2'-azo-bis-(2,4-dimethylvaleronitrile) and 2,2'-azo-bis-(2-methylbutanenitrile) was prepared; the 2,2'-azo-bis-(2,4-dimethylvaleronitrile) initiator was used at 0.7% by weight on monomers and the 2,2'-azo-bis-(2-methylbutanenitrile) initiator was used at 0.3% by weight on monomers.

The aqueous phase containing dispersant (sodium sulfate was used in place of sodium chloride as described in Example 1) was placed in a round-bottomed flask equipped with agitator. The monomer mixture was transferred to the reactor vessel and heated to 72° C. with stirring. The initiator solution was then added and the temperature was maintained at 72° C. for 2.5 hours. The temperature was raised to 90° C. and held for an additional 3 hours and then raised to 100° C. and held for another 3 hours. The solids were drained free of liquid and washed thoroughly to remove salt after cooling the reaction mixture. The washed resin was then dried at 60° C. in a convection oven and ground to a particle size of less than about 200 μ.

In this fashion, 3 different polymers were prepared crosslinked with different levels of DVB. Sample 3A contained 1 mole percent DVB, sample 3B contained 3 mole percent DVB and sample 3C contained 5 mole percent DVB.

EXAMPLE 4 (comparative)

In a manner similar to that of Example 1, a sample of crosslinked poly(dimethylaminopropylmethacrylamide) in the form of macroporous, spherical beads was prepared by copolymerizing DMAPMAM with conventional polyvinyl crosslinkers, divinylbenzene (DVB) and diethyleneglycol divinyl ether (DEGDVE).

A monomer mixture was made by mixing DMAPMAM, DVB (80% active (by weight), 20% ethylvinylbenzene), DEGDVE, 2,2'-azo-bis-(2,4-dimethylvaleronitrile) initiator (1% by weight of total monomer) and o-xylene (91% by weight on monomers). The crosslinker concentration was 4% DVB and 0.5% DEGDVE by weight of total monomer (5.7 mole percent total divinyl crosslinker).

The polymerization and polymer workup was conducted as described in Example 1, except that residual o-xylene was removed by steam sweep distillation.

EXAMPLE 5

The efficacy of the crosslinked copolymer of the present invention as a bile acid sequestrant was evaluated in beagle dogs. Beagle dogs weighing 9 to 11 kg each were fed a semi-synthetic, low cholesterol diet once per day in a quantity (200 to 300 grams/dog/day) that stabilized the body weight of the respective dogs. The semi-synthetic diet included 32.01% vitamin free casein; 43.14% dextrose; 12.42% lard; 2.39% cod liver oil; 2.72% calcium phosphate; 4.92% cella flour; and 2.39% hegsted vitamin mix No. 14.

Baseline plasma cholesterol levels were assessed for each dog by feeding the semi-synthetic diet without a bile acid sequestrant for six months and measuring plasma cholesterol levels on blood samples taken twice per week. After the baseline serum cholesterol levels were established, cholestyramine bile acid sequestrant was mixed with the diet (at dosages of 3, 6 and 12 grams/dog/day) plasma cholesterol levels were measured twice a week for four weeks to characterize the relationship between cholestyramine dosage and serum cholesterol levels for each dog.

Following derivatization of the dose/response relationship, the dogs were maintained on a regimen of 12 grams cholestyramine/dog/day until a copolymer of the present invention was substituted for the cholestyramine in the diet at a dosage of either 3 grams/dog/day or 6 grams/dog/day. The dogs were fed the copolymer of the present invention and the plasma cholesterol levels of the dogs were measured daily for four weeks. The serum cholesterol level of dog fed a bile acid sequestrant stabilizes at a level below to baseline level. The relative efficacy of the crosslinked bile acid sequestrant of the present invention and of a control dosage of 12 grams cholestyramine/day was quantified by calculating an efficacy factor ("EF") according to Equation 3:

$$EF = ((N-B)/(N-A))(12/X) \qquad [3]$$

wherein:

EF=efficacy factor

N=serum cholesterol level in milligrams cholesterol/deciliter serum (mg/dl) on the semi-synthetic diet without a bile acid sequestrant;

A=serum cholesterol level (mg/dl) or semi-synthetic diet including 12 grams cholestyramine/day;

X=(grams dosage of bile acid sequestrant of the present invention as bile acid sequestrant/day) included in serum synthetic diet; and B=serum cholesterol level (mg/dl) on semi-synthetic diet including X grams of crosslinked bile acid sequestrant of the present invention.

The sequestrant of Example 2 and Comparative Examples 3A, 3B, 3C and 4 were each tested in beagle dogs according to the above method. A sample of uncrosslinked poly(dimethylaminopropylmethacrylamide) prepared by aqueous phase solution polymerization and having a number average molecular weight of 261,000 and a weight average molecular weight of 588,000 was also tested according to this procedure and is listed as sample 5A in the table below. Results are set forth below in Table 1 as the EF, calculated according to Equation 3 for each of the sequestrants tested, along with the dosage administered, expressed as grams sequestrant per dog per day (g/dog/day) and a number (Dog No.) identifying the dog to which the dosage was administered. The results in Table 1 show that the bile acid sequestrant of the present invention (Example 2) possesses enhanced efficacy over that of sequestrants made with polyvinyl crosslinker (Examples 3A, 3B, 3C and 4) or with no crosslinker (Example 5A).

TABLE 1

| Mole Percent Divinyl Crosslinker | Mole Percent Non-Vinyl Crosslinker | Example No. | Dog No. | Dosage (g/dog/day) | EF |
| --- | --- | --- | --- | --- | --- |
| 0 | 6.5 | 2 | 205 | 3 | 4 |
| 1.0 | 0 | 3A (comparative) | 209 | 3 | 1.3 |
| 3.0 | 0 | 3B (comparative) | 206 | 3 | 1.7 |
| 5.0 | 0 | 3C (comparative) | 205 | 3 | 2.1 |

TABLE 1-continued

| Mole Percent Divinyl Crosslinker | Mole Percent Non-Vinyl Crosslinker | Example No. | Dog No. | Dosage (g/dog/day) | EF |
|---|---|---|---|---|---|
| 5.7 | 0 | 4 (comparative) | 301 | 3 | 2.7 |
| 0 | 0 | 5A (uncrosslinked) | 206 | 6 | 3.2 |

EXAMPLE 6

A suspension of particles of the sequestrant in deionized water was prepared. The suspension was serially diluted into serumless culture medium. The most concentrated suspension tested was 1000 micrograms sequestrant per milliliter suspension (μg/ml).

Exponentially growing Chinese hamster ovary (CHO) cell cultures were treated with the sequestrant dilutions for three hours. The cultures were gently rocked on a rocker platform during treatment in an attempt to maintain a uniform suspension over the cells for the entire treatment period. Negative controls, i.e., CHO cell cultures treated with serumless culture medium, and solvent controls, i.e., CHO cell cultures treated with 1% deionized water in serumless culture medium, were included.

Treatment was terminated by washing the cultures twice with Dulbecco's phosphate buffered saline and cells were allowed to recover in McCoy's 5A medium containing 10% fetal bovine serum for 0, 5 or 21 hours, i.e., 3, 8 or 24 hours from the beginning of treatment.

Cells were harvested at 3 and 24 hours by treating with trypsin-EDTA and scraping the cell monolayers from the culture flasks. The harvested cells were counted by Coulter counter to determine relative reductions in cell numbers. At selected doses, Trypan blue exclusion counts were conducted using a hemacytometer to determine cell viability to control for the possibility that some dead cells may have been counted with the Coulter counter. No cell counts were conducted at 8 hours, but the culture monolayers were examined for evidence of toxicity under an inverted microscope.

The sequestrants of Example 2 and comparative Example 5A (uncrosslinked) were each tested for cytotoxicity using the procedure set forth above. The results of cytotoxicity testing are set forth below in Table 2 as an $ED_{50}$ value in μg/ml for each sequestrant tested, wherein the $ED_{50}$ values indicate the minimum dosage of the respective sequestrant effective to kill 50% of the cells in the cell culture treated.

The results in Table 2 show that the bile acid sequestrant of the present invention (Example 2) possesses greatly reduced toxicity compared to that of a sequestrant made with no crosslinker (Example 5A). Materials with $ED_{50}$ values of 100 μg/ml or greater are generally considered non-toxic, and those with values below 100 μg/ml are considered toxic with the degree of toxicity increasing as the value of $ED_{50}$ decreases further below 100 μg/ml.

TABLE 2

| Example No. | $ED_{50}$ (μg/ml) |
|---|---|
| 2 | >100 |
| 5A | 10.0 |

We claim:

1. Water insoluble bile acid sequestrant polymer particles that have bile acid sequestering efficacy greater than that of cholestyramine, wherein the polymer particles are prepared by a process comprising:

(a) polymerizing a monomer mixture comprising amine-containing monomers by free radical polymerization and (b) non-free-radical crosslinking with a polyfunctional amine-reactive compound, provided that the amine-containing monomers contain amine functionality that is not directly attached to a vinyl group in the case where step (b) is conducted after step (a), and further provided that step (b) occurs during step (a) in the case where the monomer mixture of step (a) contains free-radical reactive polyvinyl crosslinker monomers.

2. The polymer particles of claim 1 wherein the polymer particles have amine functionality attached to polymer backbone through a side chain linkage group.

3. The polymer particles of claim 1 wherein the polymer particles are in the form of a pharmaceutically acceptable salt.

4. A pharmaceutical composition comprising:

water insoluble bile acid sequestrant polymer particles prepared by a process comprising:

(a) polymerizing a monomer mixture comprising amine-containing monomers by free radical polymerization and (b) non-free-radical crosslinking with a polyfunctional amine-reactive compound, provided that the amine-containing monomers contain amine functionality that is not directly attached to a vinyl group in the case where step (b) is conducted after step (a), and further provided that step (b) occurs during step (a) in the case where the monomer mixture of step (a) contains free-radical reactive polyvinyl crosslinker monomers, and a pharmaceutically acceptable carrier.

5. The pharmaceutical composition of claim 4 further comprising a cholesterol biosynthesis-inhibiting material.

6. The pharmaceutical composition of claim 5 wherein the cholesterol biosynthesis-inhibiting material is an HMG-CoA reductase inhibitor.

7. Water insoluble bile acid sequestrant polymer particles that have bile acid sequestering efficacy greater than that of cholestyramine and that have amine functionality attached to polymer backbone through a side chain linkage group, wherein the polymer particles are prepared by a process comprising:

(a) suspension polymerizing a monomer mixture comprising dimethylaminopropyl methacrylamide by free radical polymerization, using a dispersant to provide the polymer particles in spherical form, and (b) non-free-radical crosslinking with a substituted dihaloalkane during formation of the particles.

8. The polymer particles of claim 7 wherein the substituted dihaloalkane is used in an amount from about 2 to about 10 mole percent of the total monomers present.

9. The polymer particles of claim 8 wherein the substituted dihaloalkane is 1,3-dichloropropane or 1,3-dichloro-2-propanol.

10. The polymer particles of claim 7 wherein the polymer particles are in the form of a pharmaceutically acceptable salt having bile acid sequestering efficacy at least three times the efficacy of cholestyramine.

* * * * *